(12) United States Patent
Park et al.

(10) Patent No.: US 9,468,699 B2
(45) Date of Patent: Oct. 18, 2016

(54) AIR CONDITIONER HAVING AIR PURIFYING MODULE

(71) Applicant: SEOUL VIOSYS CO., LTD., Ansan-si, Gyeonggi-do (KR)

(72) Inventors: Jung Yeol Park, Ansan-si (KR); Young Hwan Son, Ansan-si (KR); Seong Min Lee, Ansan-si (KR); Jae Seon Yi, Ansan-si (KR); Jong Hyun Koo, Ansan-si (KR); Sang Hee Cho, Ansan-si (KR); Ju Won Yoo, Ansan-si (KR); Sung Lim Cho, Ansan-si (KR); Jong Rack Kim, Ansan-si (KR)

(73) Assignee: SEOUL VIOSYS CO., LTD., Ansan-si, Gyeonggi-do (KR)

( * ) Notice: Subject to any disclaimer, the term of this patent is extended or adjusted under 35 U.S.C. 154(b) by 0 days.

(21) Appl. No.: 14/445,277

(22) Filed: Jul. 29, 2014

(65) Prior Publication Data

US 2015/0037217 A1 Feb. 5, 2015

(30) Foreign Application Priority Data

Jul. 30, 2013 (KR) .......................... 10-2013-0090517

(51) Int. Cl.
*A61L 9/20* (2006.01)
*F24F 3/16* (2006.01)
*F25D 17/04* (2006.01)

(52) U.S. Cl.
CPC ............... *A61L 9/20* (2013.01); *F24F 3/1603* (2013.01); *F25D 17/04* (2013.01); *A61L 2209/16* (2013.01); *F24F 2003/1667* (2013.01)

(58) Field of Classification Search
CPC ........................................................ A61L 9/20
USPC ........................................................ 422/121
See application file for complete search history.

(56) References Cited

U.S. PATENT DOCUMENTS

| 5,656,242 | A | * | 8/1997 | Morrow | ................... | A61L 9/20 |
| | | | | | | 422/120 |
| 6,787,782 | B1 | * | 9/2004 | Krosney et al. | ............. | 250/436 |
| 8,834,805 | B2 | * | 9/2014 | Owen et al. | ................ | 422/186.3 |
| 2004/0170537 | A1 | * | 9/2004 | Hara | ............................. | 422/122 |
| 2007/0253860 | A1 | * | 11/2007 | Schroder | ................. | A61L 9/015 |
| | | | | | | 422/4 |
| 2008/0168790 | A1 | * | 7/2008 | Hurlebaus | ................ | A61L 9/205 |
| | | | | | | 62/331 |
| 2013/0034470 | A1 | * | 2/2013 | Wang | ................... | B01D 53/8668 |
| | | | | | | 422/121 |

FOREIGN PATENT DOCUMENTS

KR  10-2005-0056674 A  6/2005
KR  10-2005-0097603 A  10/2005

* cited by examiner

*Primary Examiner* — Kevin Joyner
*Assistant Examiner* — Holly Mull
(74) *Attorney, Agent, or Firm* — Plumsea Law Group, LLC

(57) ABSTRACT

An air conditioner including a body having an evaporator for heat-exchanging air flowing in the body, and an air purifying module coupled to the body. The air purifying module may have a light emitting diode part disposed along a flow path of the air to provide ultraviolet rays, and a filter part disposed adjacent to the light emitting diode part.

22 Claims, 6 Drawing Sheets

AIR CONDITIONER HAVING AIR PURIFYING MODULE

CROSS-REFERENCES TO RELATED APPLICATIONS

The present application claims priority under 35 U.S.C. 119(a) to Korean Application No. 10-2013-0090517, filed on Jul. 30, 2013, in the Korean Intellectual Property Office, which is herein incorporated by reference in its entirety.

BACKGROUND

1. Technical Field

Exemplary embodiments of the present disclosure relate to an air conditioner, and more particularly, to an air conditioner having an air purifying module.

2. Related Art

Recently, some countries are suffering from severe climate change as a result of global warming. For the summer seasons, the duration of air conditioner usage has increased due to heat waves, and the duration of dehumidifier usage has also increased due to long rainy seasons. For the winter seasons, the usage of a humidifier has increased due to dry air in rooms. The air conditioner, the dehumidifier, or the humidifier is a device for controlling the conditions of the indoor air, such as temperature or humidity, and utilizes physical and chemical reactions associated with evaporation and condensation phenomena of a medium.

The device for controlling the conditions of the air is referred to as an air conditioner. When the air conditioner is used for a long time, its periodic management is required. If the management, such as periodic cleaning, is not performed continuously, viruses may proliferate inside the air conditioner, or the air conditioner may give off a bad smell. Since the viruses or bad smell have a bad influence on a human body, and may also give a user an unpleasant feeling, it is necessary to avoid such problems. In addition to the method of directly cleaning the air conditioner, there is a sterilizing or deodorizing method using an ultraviolet lamp, but the method has a problem in that the ultraviolet lamp is fragile and susceptible to damage by impact. In addition, there is a sterilizing and deodorizing method using an on generating device, but the ozone generating device may generate harmful ozone. Therefore, a new air purifying method to improve the sterilizing and deodorizing efficiency is still desired.

SUMMARY

This summary is intended to provide an overview of the subject matter of this patent, and is not intended to identify essential elements or key elements of the subject matter, nor is it intended to be used to determine the scope of the claimed embodiments. The proper scope of this patent may be ascertained from the claims set forth below in view of the detailed description below and the drawings.

An embodiment of the present disclosure relates to an air conditioner having an air purifying module that can effectively perform a sterilizing and deodorizing function.

In one embodiment, an air conditioner may include a body including an evaporator for heat-exchanging air flowing therein, and an air purifying module coupled to the body. The air purifying module may have a light emitting diode part disposed along a flow path of the air to provide ultraviolet rays, and a filter part disposed adjacent to the light emitting diode part.

In another embodiment, an air conditioner may include a body including an air circulation unit generating a flow of air therein, and an air purifying module coupled to the body. The air purifying module may have a light emitting diode part disposed along a flow path of the air to provide ultraviolet rays, and a filter part disposed adjacent to the light emitting diode part.

According to embodiments disclosed herein, the air conditioner may include an air purifying module capable of effectively performing a sterilization function and a deodorization function for flowing air, thereby improving the cleanliness of the indoor air.

BRIEF DESCRIPTION OF THE DRAWINGS

The above and other aspects, features, and other advantages will be more clearly understood from the following detailed description taken in conjunction with the accompanying drawings, in which.

DETAILED DESCRIPTION OF EMBODIMENTS

Figure 1:
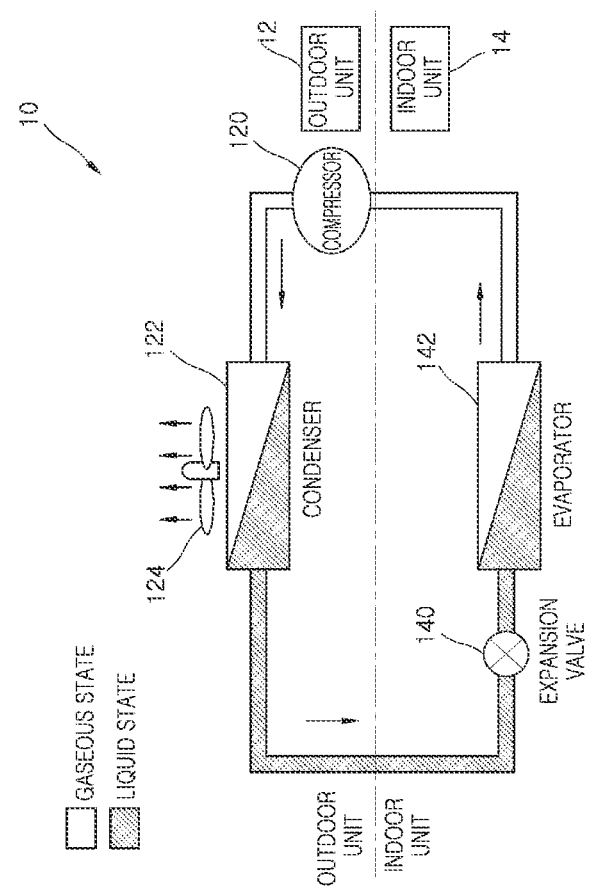
FIG. 1 is a schematic diagram illustrating an air conditioner according to an embodiment of the present disclosure.

Hereinafter, embodiments of the present disclosure will be described with reference to accompanying drawings. However, the embodiments are for illustrative purposes only and are not intended to limit the scope of the disclosure. For clarity, the detailed descriptions herein describe certain exemplary embodiments, but the disclosure in this application may be applied to any air conditioner comprising certain of the features described herein and recited in the claims. In particular, although the following detailed description describes certain exemplary embodiments of air conditioners, it should be understood that other embodiments may have different structures, forms, and configurations. The drawings may not be to scale, and the widths, lengths, and thicknesses shown may be exaggerated for clarity.

In addition, in the description, the terms "first", "second" and so on are used to distinguish one element from another element, but are not to be construed to limit the elements. Also, the phrase "positioned over any member" or "positioned on an upper or lower part or a lateral surface" refers to a relative positional relation, and does not limit a specific case where it comes into directly contact with the member, or another member is further interposed between the interfaces. Further, the phrase "one element is connected to another element" or "one element is provided on another element" means that one element is directly connected to other element, or a connection relation in which a separate element is interposed therebetween can be achieved. Throughout the drawings, like reference numerals refer to like elements, and redundant descriptions are omitted.

FIG. 1 is a diagram schematically illustrating an air conditioner according to an embodiment of the present disclosure. Specifically, an air conditioner 10 is an air conditioning system. The air conditioner 10 according to the embodiment of the present disclosure may include an outdoor unit 12 and an indoor unit 14. The outdoor unit 12 may have a compressor 120, a condenser 122, and a blower 124. The indoor unit 14 may have an expansion valve 140 and an evaporator 142.

First, the configuration of the outdoor unit 12 will be described. In an embodiment, the compressor 120 may suck a gaseous refrigerant of low temperature and low pressure, which is evaporated by the evaporator 142. The gaseous refrigerant may be discharged in a state in which the pressure of the gaseous refrigerant is increased. The condenser 122 may heat-exchange the gaseous refrigerant of the high temperature and high pressure with surrounding air or cooling water to discharge the heat from the gaseous refrigerant. The condenser may receive the heat from the gaseous refrigerant, so that the gaseous refrigerant is condensed and liquefied. The air heated by the heat discharged during the process may be discharged outwardly by the blower 124. The liquefied refrigerant may be fed to the indoor unit 14. The expansion valve 140 may serve to lower the pressure of the liquefied refrigerant. This is to cause the evaporation to easily occur in the evaporator. The evaporator 142 evaporates the liquefied refrigerant of the low temperature and low pressure that passes the expansion valve 140, and the evaporated refrigerant heat-exchanges the indoor air with the heat. Subsequently, the evaporated refrigerant subjected to the heat exchange may flow to the compressor 120. By the above-described circulation of the refrigerant, the refrigerant evaporated in the evaporation 142 may serve to lower the temperature of the indoor air.

Figure 2A:
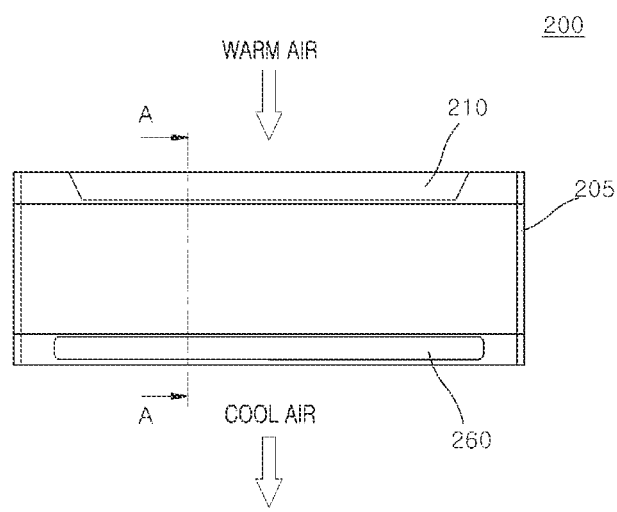
FIG. 2A is a schematic diagram illustrating an air conditioner according to a first embodiment of the present disclosure.
Figure 2B:
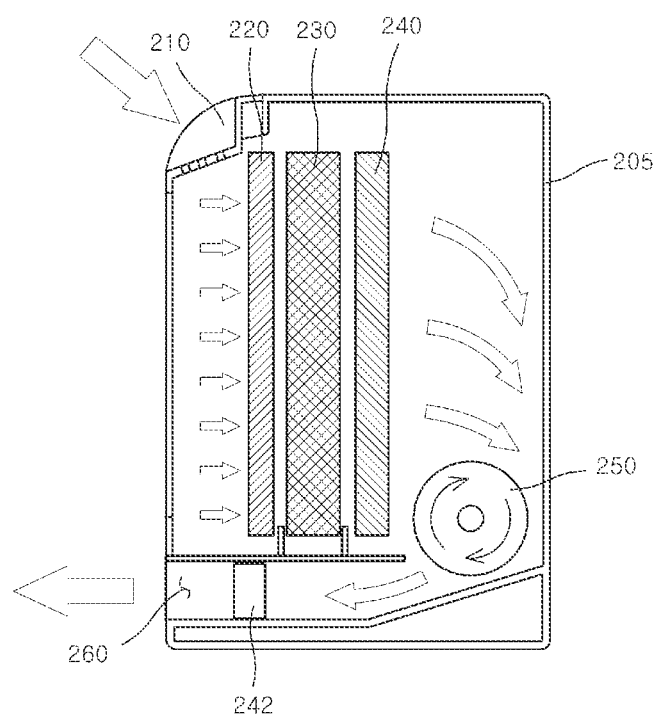
FIG. 2B is a schematic diagram illustrating a cross sectional view of the air conditioner of FIG. 2A taken along the line A-A of FIG. 2A.

FIG. 2A is a view schematically illustrating an air conditioner according to a first embodiment of the present disclosure. FIG. 2B is a cross sectional view of the air conditioner of FIG. 2A taken along the line A-A in FIG. 2A, Referring to FIGS. 2A and 2B, an air conditioner 200 may include a body 205 forming a frame, and air purifying modules 240 and 242 coupled to the body 205. The body 205 may be an indoor unit for a wall-mounted air conditioner, for example.

The body 205 may have an air inlet port 210, a filter 220, an evaporator 230, an air circulation unit 250, and an air outlet port 260. An air flow path may be formed from the air inlet port 210 to the air outlet port 260 in the body 205 by the air circulation unit 250. That is, fine particles contained in the indoor air fed from the air inlet port 210 may be filtered by the filter 220, and then the filtered air may be fed to the evaporator 230. The fed air may transfer heat to the refrigerant evaporated by the evaporator 230, thereby lowering the temperature of the fed air. The lower-temperature air may then be discharged indoors via the air outlet port 260. By repetition of the above process, the air conditioner 200 of this embodiment can lower the indoor temperature. Alternatively, the air circulation unit 250 of this embodiment may include a rotor. The air circulation unit 250 can guide the flow of the air toward the air outlet port 260 in the body 105 by the self-rotation.

The air purifying modules 240 and 242 may perform sterilization and deodorization for the air fed into the body 205. As one embodiment, the first air purifying module 240 of the air purifying modules 240 and 242 may be interposed between the evaporator 230 and the air circulation unit 250. The second air purifying module 242 may be interposed between the air circulation unit 250 and the air outlet port 260. The first air purifying module 240 may be disposed adjacent to the evaporator 230, and thus may have a configuration and size corresponding to those of the evaporator 230. The second air purifying module 240 may be disposed adjacent to the air outlet port 260, and thus may have a configuration and size corresponding to the duct connected to the air outlet port 260. As illustrated, since the first air purifying module 240 may have a relatively large volume, the air purifying efficiency is advantageously increased. The second air purifying module 242 can be configured to have a small volume relative to the first air purifying module 240. In some examples, the air conditioner may include only the first aft purifying module 240 in the body 205, or may include only the second air purifying module 242 in the body 205.

The air purifying modules 240 and 242 of this embodiment may be disposed at a rear end of the evaporator 230. In this manner, the air purifying modules 240 and 242 can sterilize and deodorize the air passing the evaporator 230. In general, the air passing the evaporator 230 may have a lower humidity relative to the air at a front end of the evaporator 230. The lower humidity may provide a relatively dry environment for filters and light emitting diodes of the air purifying modules 240 and 242, thereby extending the lifespans of the air purifying modules 240 and 242.

Figure 3:
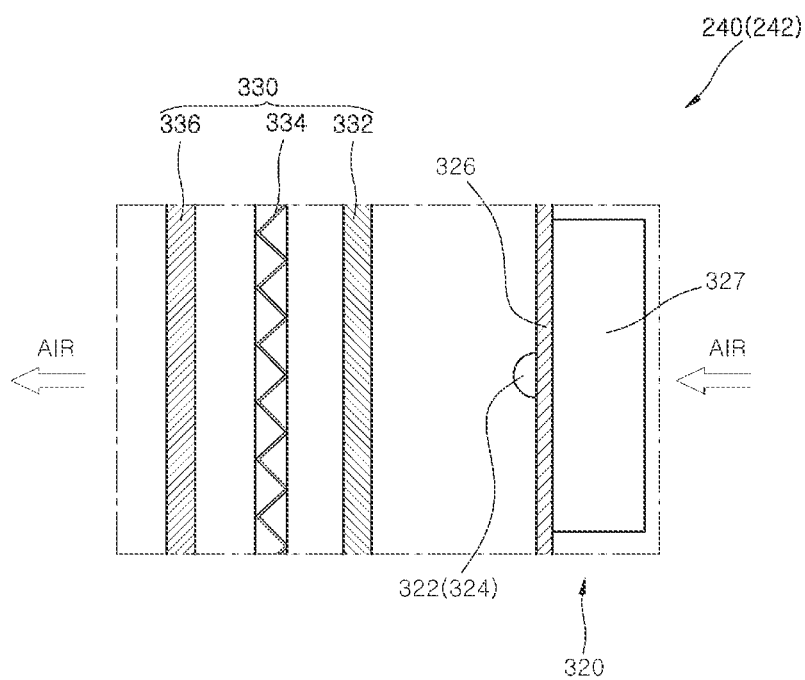
FIG. 3 is a schematic diagram illustrating an air purifying module according to an embodiment of the present disclosure.

FIG. 3 is a view schematically illustrating an air purifying module according to an embodiment of the present disclosure. As shown, the air purifying modules 240 and 242 may include a light emitting diode part 320 providing ultraviolet rays and a filter part 330. The light emitting diode part 320 may be disposed over a heat sink 327 with an opening (not illustrated) through which the air passes. The light emitting diode part 320 may have a support member 326 with an opening corresponding to the opening of the heat sink 327. A sterilization light emitting diode 322 and a photocatalytic light emitting diode 324 may be disposed on the support member 326.

The light emitting diode part 320 and the filter part 330 may be arranged to correspond to the flow path of the air, which is illustrated in FIG. 3. That is, the light emitting diode part 320 and the filter part 330 may be disposed so that a direction of the ultraviolet rays emitted from the light emitting diode part 320 is identical to a flow direction of the air in the body 205. The filter part 330 may have a photocatalytic filter 332 and a collection filter 334, which may be disposed in order from the light emitting diode part 320. The filter part 330 may further have a carbon filter 336 for deodorization at a rear end of the collection filter 334.

The light emitting diode part 320 may have the sterilization light emitting diode 322 emitting ultraviolet rays to destroy germs, and the photocatalytic light emitting diode 324 emitting ultraviolet rays to react with the photocatalytic filter 332. The sterilization light emitting diode 322 may emit ultraviolet rays of about 200 to 300 nm, for example, and the photocatalytic light emitting diode 324 may emit ultraviolet rays of about 300 to 400 nm, for example. In embodiments, the light emitting diodes may be classified as photocatalytic light emitting diodes or as sterilization light emitting diodes, and may be arranged according to the functions of the light emitting diodes. In some embodiments, such classifications may not apply, and the light emitting diodes may serve multiple functions. That is, the photocatalytic light emitting diode may perform a sterilization function, and the sterilization light emitting diode may have a photocatalytic reaction together with the photocatalytic filter.

Explaining the method of driving the air purifying module according to the above-described embodiment, the air passing the evaporator 230 may be fed to the air purifying modules 240 and 242. While the fed air passes the air purifying modules 240 and 242, germs contained in the air can be sterilized (e.g., destroyed, killed, otherwise inactivated) by the ultraviolet rays emitted from the sterilization light emitting diode 322. Otherwise, the germs contained in the air can be collected by the collection filter 334, and then can be sterilized by the ultraviolet rays emitted from the sterilization light emitting diode 322 in the collected state. The collection filter 334 may collect the germs contained in the moving air to assist the sterilization light emitting diode 322 in improving the sterilization function. The collection filter 334 may be, for example, a cabin filter as is known in the art.

Odors may be removed from the moving air by a photocatalytic reaction between ultraviolet rays emitted from the photocatalytic light emitting diode 324 and the photocatalytic filter 332. In addition, odors may be further removed from moving air when it passes the carbon filter 336 located at the rear end. Although not illustrated, the filter part 330 may have various other functional filters, which can be commercially available.

Explaining the configuration of the filter part 330 in detail is with reference to the accompanying drawings, the photocatalytic filter 332, the collection filter 334, and the carbon filter 336 may be sequentially arranged from the light emitting diode part 320, with the photocatalytic filter 332 being closest, the carbon filter 336 being farthest, and the collection filter 334 being in between the photocatalytic filter 332 and carbon filter 336.

The photocatalytic filter 332 may contain a substance providing the photocatalytic reaction as a photocatalytic medium. For example, the photocatalyst may include titanium nitride $TiO_2$, silicon oxide $SiO_2$, tungsten oxide $WO_3$, and zirconium oxide ZnO. The photocatalytic filter 332 may be formed in a layered structure having titanium nitride $TiO_2$ The photocatalytic filter 332 may be made of a material, through which the air flows, like metal foam or a porous metallic material, coated with the above substance.

The photocatalytic filter 332 can have a photocatalytic reaction with ultraviolet rays of about 300 to 400 nm emitted from the photocatalytic light emitting diode 324. If the ultraviolet rays are absorbed by the photocatalytic medium, electrons ($e^-$) and electron holes (+) may be generated on the surface thereof, and the electrons may react with oxygen on the surface of the photocatalytic medium to generate superoxide anions (O2-). In addition, the electron holes may react with moisture contained in air to generate hydroxyl radical (OH—), and organic substances may be subjected to oxidation decomposition by the hydroxyl radial generated at this time. Therefore, the polluted substances and the bad odor substances contained in the air fed into the air purifying unit may be decomposed to be converted into water and carbon dioxide. The photocatalytic filter 332 can perform the deodorization function for the fed air in cooperation with the photocatalytic light emitting diode 324.

The collection filter 334 may perform a function of collecting the germs contained in the fed air. To that end, the collection filter 334 may have micropores so that the germs do not easily pass. The collection filter 334 may have a filter substance of a folded shape in the flow direction of the air, as illustrated in FIG. 3, in order to increase the collection amount per unit area by increasing the surface area thereof. Germs collected by the collection filter 334 may be sterilized by ultraviolet rays of about 200 to 300 nm emitted from the sterilization light emitting diode 322. The collection filter 334 may increase a time for which germs contained in the air are exposed to the sterilization ultraviolet rays, thereby increasing the sterilization efficiency of the sterilization light emitting diode 322.

The carbon filter 336 may be disposed at the rear end of the collection filter 334. The carbon filter 336 may contain activated carbon and a catalyst to filter the organic chemical substances contained in the air while the air passes the carbon filter 336. Therefore, the carbon filter can perform the deodorization function for the fed air. In embodiments, the carbon filter 336 may be provided together with the photocatalytic filter 332 and the photocatalytic light emitting diode 324, thereby increasing the deodorization efficiency of the air purifying unit. In addition, the carbon filter 336 may have a drawback in that it has limited durability and thus a short lifespan. Therefore, carbon filter 336 is disposed at the rear end of the photocatalytic filter 332 to extend the lifespan of the carbon filter 336.

Although not illustrated in FIG. 3, the filter part 330 may have various functional filters. For example, the functional filters may include a high-efficiency particulate air (HEPA) filter, a deodorization filter, an antibacterial filter, and an allergen filter.

Figure 4:
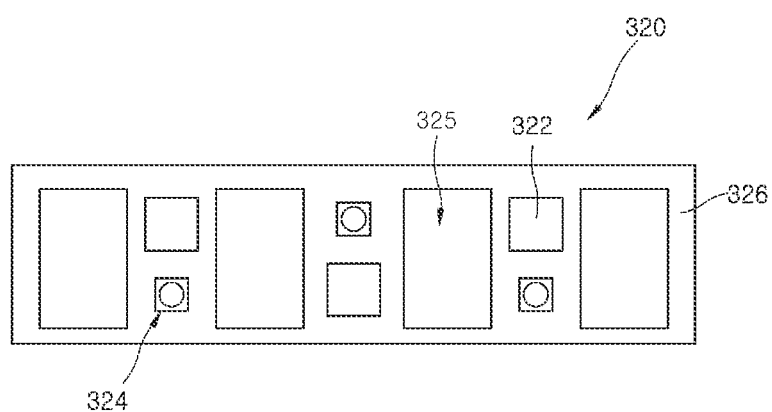
FIG. 4 is a schematic diagram illustrating a light emitting diode part according to an embodiment of the present disclosure.

FIG. 4 is a view schematically illustrating a light emitting diode part according to an embodiment of the present disclosure. Referring to FIG. 4, the light emitting diode part 320 may have sterilization light emitting diodes 322 and photocatalytic light emitting diodes 324, which are disposed on a support member 326 having openings 325. Openings 325 formed in the support member 326 may coincide with the position of openings formed in the heat sink 327, so that the air flows.

Again referring to FIG. 4, sterilization light emitting diodes 322 and photocatalytic light emitting diodes 324 may be disposed on support member 326, with openings 325 being interposed between the diodes. As illustrated, sterilization light emitting diodes 322 and photocatalytic light emitting diodes 324 may be disposed in pairs. However, the present disclosure is not limited thereto, and a pair of sterilization light emitting diodes 322 may exist in one region, and a pair of photocatalytic light emitting diodes 324 may exist in another region.

The sterilization light emitting diode 322 and the photocatalytic light emitting diode 324 may emit light concurrently by a control device (not illustrated), or any one of the sterilization light emitting diodes 322 and the photocatalytic light emitting diodes 324 may emit the light. If any one of the sterilization light emitting diodes 322 and the photocatalytic light emitting diodes 324 selectively emits the light, any one of the sterilization or deodorization reaction is selectively performed.

Figure 5A:
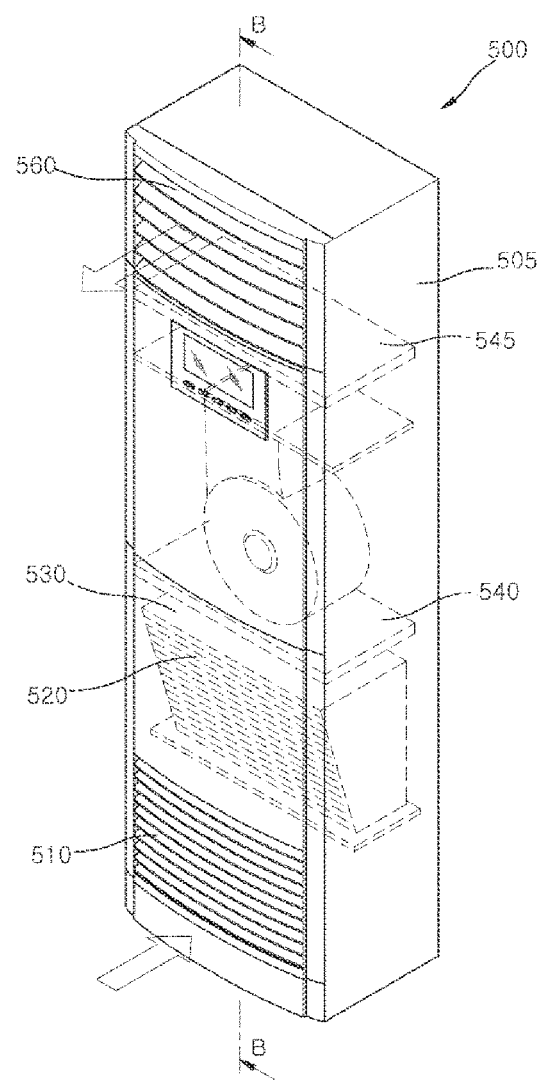
FIG. 5A is a schematic diagram illustrating an air conditioner according to a second embodiment of the present disclosure.
Figure 5B:
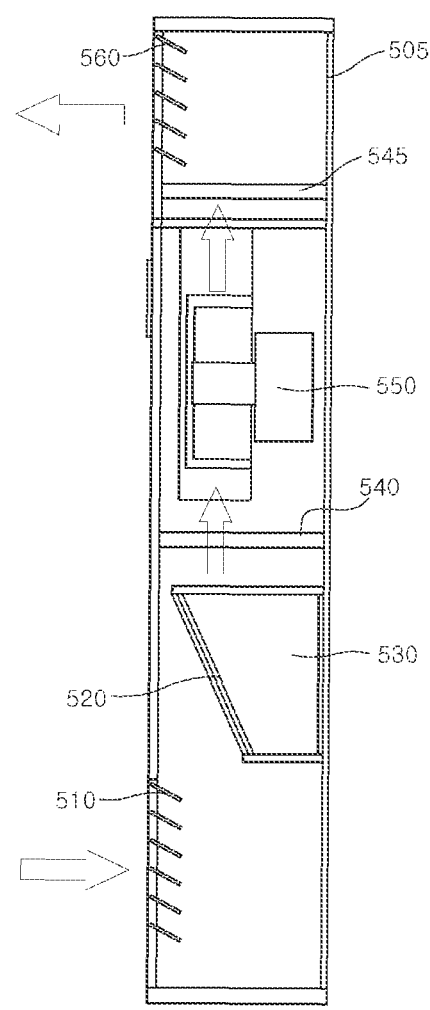
FIG. 5B is a schematic diagram illustrating a cross sectional view of the air conditioner of FIG. 5A taken along the line A-A of FIG. 5A.

FIG. 5A is a view schematically illustrating an air conditioner according to a second embodiment of the present disclosure. FIG. 5B is a cross sectional view of the air conditioner of FIG. 5A taken along the line A-A of FIG. 5A.

Referring to FIGS. 5A and 5B, an air conditioner 500 may include a body 505 forming a frame, and air purifying modules 540 and 545 coupled to the body 505. The body 505 may be an indoor unit for a stand-type air conditioner, for example. The air purifying modules 540 and 545 may be a first air purifying module 540 and a second air purifying module 545, which are named according to the positions of the modules in body 505.

As illustrated, body 505 may have an air inlet port 510 formed at a rear end part for the purpose of the inflow of air. While the air fed into the body 505 via the air inlet port 510 may flow to an upper part, the fine particles may be filtered by a filter 520. The air passing the filter 520 may be fed to an evaporator 530. The air may be heat-exchanged in the evaporator 530, and then may be discharged in a state in which the temperature is lowered. Subsequently, the air may be sterilized and/or odorized while the air passes the first air purifying module 540. Then, the sterilized and/or odorized air may flow upwardly by an air circulation unit 550. The air circulation unit 550 may be a blower, for example. The air flowing to the upward part by the air circulation unit 550 may be again sterilized and/or odorized while passing the second air purifying module 545. The re-sterilized and/or re-deodorized air may be discharged outwardly from the body 505 via an air outlet port 560 formed in an upper end of the body 505. In this way, the indoor air of the relatively high temperature fed through the air inlet port 510 may be converted into the low temperature state through the evaporator 530, and may be sterilized and/or deodorized through the first and second air purifying modules 540 and 545. The first air purifying module 540 may be interposed between the evaporator 530 and the air circulation unit 550, and the second air purifying module 550 may be interposed between the air circulation unit 550 and the air outlet port 560.

In some embodiments, the air conditioner may include any one of the first air purifying module 540 and the second air purifying module 545.

The air purifying modules 540 and 545 may have a light emitting diode part providing ultraviolet rays, and a filter part. The configurations of the air purifying modules 540 and 545 may be substantially identical to those of the air purifying modules 240 and 242 described in detail with reference to FIGS. 3 and 4, and thus the detailed description will be omitted to avoid repetition.

As described above, an air conditioner according to embodiments of the present disclosure may include the air purifying module. The air purifying module effectively carries out the sterilization function and the deodorization function for the air flowing therein, thereby improving the cleanliness of the indoor air. The air purifying module of the present disclosure can be applied to various air conditioners requiring air circulation or air purification, such as heaters, dehumidifiers, humidifiers, or automotive air conditioners. That is, the air conditioner of the present disclosure can have various applications satisfying the condition in which the body has the air purifying unit generating the flow of the air fed thereto, and the air purifying module is coupled to the body.

In embodiments of the present disclosure, the air purifying module may have an ultraviolet light emitting diode emitting the ultraviolet rays for the purpose of the sterilization and deodorization functions. The ultraviolet light emitting diode can be smaller and more durable than conventional ultraviolet lamps employing thermoelectrons and a luminous substance. In addition, the lifespan of the light emitting diode is advantageously long in view of the properties of light emitting diodes.

The embodiments of the present disclosure have been disclosed above for illustrative purposes. Those skilled in the art will appreciate that various modifications, additions, and substitutions are possible, without departing from the scope and spirit of the inventive concept as disclosed in the accompanying claims, and their equivalents.

Further, in describing embodiments, the specification may have presented methods and/or processes as particular sequences of steps. However, to the extent that the methods or processes do not rely on the particular order of steps set forth herein, the methods or processes should not be limited to the particular sequences of steps described. As one of ordinary skill in the art would appreciate, other sequences of steps may be possible. Therefore, the particular order of the steps set forth in the specification should not be construed as limitations on the claims. In addition, the claims directed to the methods and/or processes should not be limited to the performance of their steps in the order written, and one skilled in the art can readily appreciate that the sequences may be varied.

What is claimed is:

1. An air conditioner comprising:
  a body including an evaporator for heat-exchanging air flowing in the body;
  a first air purifying module and a second air purifying module, each coupled to the body,
  wherein each air purifying module includes:
    a light emitting diode part disposed along a flow path of the air to provide ultraviolet rays, and
    a filter part disposed adjacent to the light emitting diode part, and
  wherein the first air purifying module is disposed at a rear end of the evaporator; and
  an air circulation unit disposed at a rear end of the first air purifying module,
  wherein the second air purifying module is disposed at a rear end of the air circulation unit,
  wherein the first air purifying module has a volume larger than a volume of the second air purifying module, and
  wherein the light emitting diode part comprises:
    a support member spanning the each air purifying module substantially perpendicular to the flow path of the air and defining a first opening, a second opening, a third opening, and a fourth opening;
    a first sterilization light emitting diode disposed on the support member in between the first opening and the second opening;
    a first photocatalytic light emitting diode disposed on the support member in between the first opening and the second opening,
    a second sterilization light emitting diode disposed on the support member in between the second opening and the third opening;
    a second photocatalytic light emitting diode disposed on the support member in between the second opening and the third opening;
    a third sterilization light emitting diode disposed on the support member in between the third opening and the fourth opening; and
    a third photocatalytic light emitting diode disposed on the support member in between the third opening and the fourth opening,
    wherein the first sterilization light emitting diode, the second photocatalytic light emitting diode, and the third sterilization light emitting diode are disposed on a first side of the support member, and
    wherein the first photocatalytic light emitting diode, the second sterilization light emitting diode, and the third photocatalytic light emitting diode are disposed on a second side of the support member opposite to the first side of the support member.

2. The air conditioner of claim 1, wherein the filter part includes a photocatalytic filter and a collection filter, wherein the photocatalytic filter is disposed downstream of the light emitting diode part and upstream of the collection filter, and wherein the light emitting diode part emits the ultraviolet rays in a direction substantially the same as the flow of the air and toward the photocatalytic filter.

3. The air conditioner of claim 2, wherein the filter part further includes a carbon filter disposed downstream of the collection filter to perform a deodorization function.

4. The air conditioner of claim 2, wherein the first photocatalytic light emitting diode acts with the photocatalytic filter, and the first sterilization light emitting diode removes germs collected by the collection filter.

5. The air conditioner of claim 4, wherein the first photocatalytic light emitting diode emits ultraviolet rays of about 300 to 400 nm, and the first sterilization photocatalytic light emitting diode emits ultraviolet rays of about 200 to 300 nm.

6. The air conditioner of claim 1, wherein each air purifying module is disposed so that a direction of the ultraviolet rays emitted from the light emitting diode part is identical to a flow direction of the air in the body.

7. The air conditioner of claim 1, wherein the body includes an air inlet port, a filter disposed downstream of the air inlet port, wherein the evaporator is disposed downstream of the filter, wherein the air circulation unit draws air into the body, and an air outlet port disposed downstream of the second air purifying module, and wherein the flow path of the air extends from the air inlet port to the air outlet port.

8. The air conditioner of claim 7, wherein the air circulation unit includes one of a rotor and a blower.

9. The air conditioner of claim 1, wherein the body is one of an indoor unit for a wall-mounted air conditioner and an indoor unit for a stand-type air conditioner.

10. The air conditioner of claim 1, wherein the each air purifying module further comprises a heat sink disposed upstream of the light emitting diode part, and
wherein the heat sink defines a first opening, a second opening, a third opening, and a fourth opening that coincide, respectively, with the first opening, the second opening, the third opening, and the fourth opening of the support member of the light emitting diode part.

11. The air conditioner of claim 1, wherein the first sterilization light emitting diode and the first photocatalytic light emitting diode emit light concurrently.

12. The air conditioner of claim 1, wherein at least one of the first sterilization light emitting diode, the second sterilization light emitting diode, the third sterilization light emitting diode, the first photocatalytic light emitting diode, the second photocatalytic light emitting diode, and the third photocatalytic light emitting diode selectively emits light.

13. An air conditioner comprising:
a body including an air circulation unit generating a flow of air therein; and
a first air purifying module and a second air purifying module, each coupled to the body,
wherein each air purifying module has:
a light emitting diode part disposed along a flow path of the air to provide ultraviolet rays, and
a filter part disposed adjacent to the light emitting diode part,
wherein the first air purifying module is disposed upstream of the air circulation unit,
wherein the second air purifying module is disposed downstream of the air circulation unit,
wherein the first air purifying module has a volume larger than a volume of the second air purifying module, and
wherein the light emitting diode part comprises:
a support member spanning the each air purifying module substantially perpendicular to the flow path of the air and defining a first opening, a second opening, and a third opening,
a first sterilization light emitting diode disposed on the support member in between the first opening and the second opening,
a first photocatalytic light emitting diode disposed on the support member in between the first opening and the second opening,
a second sterilization light emitting diode disposed on the support member in between the second opening and the third opening, and
a second photocatalytic light emitting diode disposed on the support member in between the second opening and the third opening,
wherein the first sterilization light emitting diode and second photocatalytic light emitting diode are disposed on a first side of the support member, and
wherein the first photocatalytic light emitting diode and the second sterilization light emitting diode are disposed on a second side of the support member opposite to the first side of the support member.

14. The air conditioner of claim 13, wherein the air circulation unit includes one of a rotor and a blower.

15. The air conditioner of claim 13, wherein the body includes an air inlet port, wherein the air circulation unit is disposed downstream of the air inlet port, and an air outlet port disposed downstream of the second air purifying module, and wherein the flow path of the air extends from the air inlet port to the air outlet port.

16. The air conditioner of claim 15, further comprising an evaporator disposed downstream of the air inlet port and upstream of the first air purifying module.

17. The air conditioner of claim 13, wherein the filter part includes a photocatalytic filter and a collection filter, wherein the photocatalytic filter is disposed downstream of the light emitting diode part and upstream of the collection filter, and wherein the light emitting diode part emits the ultraviolet rays in a direction substantially the same as the flow of the air and toward the photocatalytic filter.

18. The air conditioner of claim 17, wherein the filter part further includes a carbon filter disposed downstream of the collection filter to perform a deodorization function.

19. The air conditioner of claim 17, wherein the first photocatalytic light emitting diode acts with the photocatalytic filter, and the first sterilization light emitting diode removes germs collected by the collection filter.

20. The air conditioner of claim 19, wherein the first photocatalytic light emitting diode emits ultraviolet rays of about 300 to 400 nm, and the first sterilization photocatalytic light emitting diode emits ultraviolet rays of about 200 to 300 nm.

21. The air conditioner of claim 13, wherein the each air purifying module further comprises a heat sink disposed upstream of the light emitting diode part, and
wherein the heat sink defines a first opening, a second opening, and a third opening that coincide, respectively, with the first opening, the second opening, and the third opening of the support member of the light emitting diode part.

22. The air conditioner of claim 13, wherein at least one of the first sterilization light emitting diode, the second sterilization light emitting diode, the first photocatalytic light emitting diode, and the second photocatalytic light emitting diode selectively emits light.

* * * * *